(12) United States Patent
Matzger et al.

(10) Patent No.: US 9,096,530 B2
(45) Date of Patent: Aug. 4, 2015

(54) CRYSTALLINE EXPLOSIVE MATERIAL

(75) Inventors: Adam Matzger, Ann Arbor, MI (US); Onas Bolton, Dearborn, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 201 days.

(21) Appl. No.: 13/368,965

(22) Filed: Feb. 8, 2012

(65) Prior Publication Data
US 2012/0305150 A1 Dec. 6, 2012

Related U.S. Application Data

(60) Provisional application No. 61/440,699, filed on Feb. 8, 2011, provisional application No. 61/510,276, filed on Jul. 21, 2011.

(51) Int. Cl.
| | | |
|---|---|---|
| *C06B 25/34* | (2006.01) |
| *C07D 235/02* | (2006.01) |
| *C06B 31/28* | (2006.01) |
| *C06B 33/08* | (2006.01) |
| *C06B 45/34* | (2006.01) |
| *C06B 45/18* | (2006.01) |
| *C06B 45/24* | (2006.01) |
| *C06B 21/00* | (2006.01) |

(52) U.S. Cl.
CPC .......... *C07D 235/02* (2013.01); *C06B 21/0066* (2013.01); *C06B 25/34* (2013.01); *C06B 31/28* (2013.01); *C06B 33/08* (2013.01); *C06B 45/18* (2013.01); *C06B 45/24* (2013.01); *C06B 45/34* (2013.01)

(58) Field of Classification Search
CPC ........ C06B 31/28; C06B 33/08; C06B 45/18; C06B 45/34; C06B 45/24
See application file for complete search history.

(56) References Cited

U.S. PATENT DOCUMENTS

2005/0199323 A1 9/2005 Nielson et al.
2006/0219341 A1* 10/2006 Johnston et al. ................ 149/46

OTHER PUBLICATIONS

Bolton et al., "Improved Stability and Smart-Material Functionality Realized in an Energetic Cocrystal", Angew. Chem. Int. Ed. 2011, 50, 8960-8963.
Bolton et al., "Improved Stability and Smart-Material Functionality Realized in an Energetic CoCrystal", Supporting Information, Angewandte Chemie, Wiley-VCH 2011, pp. 6.
Kholod et al., "An analysis of stable forms of CL-20: A DFT study of conformational transitions, Infrad and Raman Spectra", Science Direct, Elsevier B.V., 2007, pp. 14-25.
Talawar et al., "Establishment of process technology for the manufacture of dinitrogen pentoxide and its utility for the synthesis of most powerful explosive of today CL 20", Elsevier, Journal of Hazardous Materials, B124, 2005, pp. 153-164.
Nielsen et al., "Synthesis of Polyazapolycyclic Caged Polynitramines, Pergamon", Tetrahedron 54, 1998, pp. 11793-11812.
International Application No. PCT/US2012/024327, International Search Report mailed Sep. 27, 2012, pp. 1-6.
Written Opinion of PCT/US2012/024327 mailed Sep. 27, 2012, pp. 1-7.

* cited by examiner

*Primary Examiner* — Aileen B Felton
(74) *Attorney, Agent, or Firm* — Harness, Dickey & Pierce, P.L.C.

(57) ABSTRACT

An explosive material in the form of a cocrystal comprising 2,4,6,8,10,12-hexanitro-2,4,6,8,10,12-hexaazaisowurtzitane (CL-20 or HNIW) and at least one energetic material. The energetic material is selected from 2,4,6-trinitrotoluene (TNT), and 1,3,5,7-tetranitro-1,3,5,7-tetrazocane (HMX).

18 Claims, 12 Drawing Sheets

CRYSTALLINE EXPLOSIVE MATERIAL

CROSS-REFERENCE TO RELATED APPLICATIONS

This application claims the benefit of U.S. Provisional Application No. 61/440,699, filed on Feb. 8, 2011 and U.S. Provisional Application No. 61/510,276, filed on Jul. 21, 2011. The entire disclosures of each of the above applications are incorporated herein by reference.

GOVERNMENT SUPPORT

This invention was made with government support under HDTR1-09-1-0033 awarded by The Defense Threat Reduction Agency ("DTRA"). The Government has certain rights in the invention.

BACKGROUND

The present disclosure relates to a high explosive energetic cocrystalline material for use in munitions, propellant, and demolition applications.

2,4,6,8,10,12-Hexanitro-2,4,6,8,10,12-hexaazaisowurtzitane (CL-20 or HNIW), is a high density, high oxygen balance energetic developed by the U.S. Navy. The high explosive compound has a high detonation velocity (and thus is a strong explosive) and generates a low signal (less ash/smoke—due in large part to its high oxygen balance), but is still struggling to find commercial and military use. The principal drawback of CL-20 is its relatively poor impact shock sensitivity, particularly as compared to high melting explosive (HMX), the current state-of-the-art military explosive. CL-20 is more sensitive to impact than HMX, making it unsuitable for some applications and U.S. Military specifications.

Although not limited by theory, the crystal structure of energetic materials has a significant effect on their performance and stability. Detonation velocity, the velocity of the shock wave produced on detonation, is a direct measurable to the explosive power of the material. This is related to the speed of sound in the energetic crystal, over which the density and quality of the crystal has great influence. Mixed compositions and formulations will inevitably have inhomogeneities that disrupt the path of the shockwave, leading to lower detonation velocity. Brisance, the speed at which an explosive reaches its maximum pressure, is another performance measurable also closely related, for the same reasons, to density and homogeneity. Brisance is often thought of as the "shattering power" of the explosive.

There is a continuing need for explosive materials that combine the advantages and avoid the drawbacks of known compositions.

SUMMARY

A crystalline material contains both CL-20 and at least one energetic material. In one embodiment, the material is a cocrystal, wherein molecules of the components combine on an ordered molecular basis to create a material of homogeneous density. In one aspect, the crystalline material contains both CL-20 and 2,4,6-trinitotoluene (TNT) in a 1:1 molar ratio and is characterized by a conversion to its pure components at about 135° C. The cocrystal also exhibits characteristic X-ray diffraction pattern peaks, as well as a distinctive Raman spectrum and infrared absorption spectrum.

In another embodiment, the crystalline material contains both CL-20 and 1,3,5,7-tetranitro-1,3,5,7-tetrazocane (HMX) in a 2:1 molar ratio and is characterized by a melting/decomposition with an onset of about 235° C. The cocrystal also exhibits characteristic X-ray diffraction pattern peaks, as well as a distinctive Raman spectrum and infrared absorption spectrum.

The cocrystalline material containing both CL-20 and TNT has properties that make it superior in some applications to simple mixtures or formulations of its two components. For example, the 1:1 CL-20:TNT cocrystal is significantly more insensitive than mixtures of its two components.

The compositions of the invention are synthesized in a number of procedures, for example by combining the components into solution at certain ratios and allowing the solution to slowly evaporate. In various embodiments, the crystalline material is a component of an explosive composition containing the cocrystal and one or more conventional explosive materials.

DRAWINGS

The drawings described herein are for illustrative purposes only of selected embodiments and not all possible implementations, and are not intended to limit the scope of the present disclosure.

FIGS. 3a-3d show a molecular model of the cocrystal of CL-20 and TNT;

FIGS. 8a-8d show a molecular model of the cocrystal of CL-20 and HMX;

Corresponding reference numerals indicate corresponding parts throughout the several views of the drawings.

DETAILED DESCRIPTION

For the first time, the present application combines two established energetic compounds into one heretofore unknown cocrystalline material. In various embodiments, 2,4,6,8,10,12-hexanitro-2,4,6,8,10,12-hexaazaisowurtzitane (CL-20) combines with at least one energetic material to form a cocrystal. The cocrystal is formed on an ordered atomic basis to create a new phase of homogenous density.

In various embodiments, the energetic material is selected from 5-nitro triazol-3-one (NTO), 2,4,6-trinitrotoluene (TNT), 1,3,5,7-tetranitro-1,3,5,7-tetrazocane (HMX), trinitro triamino benzene (TATB), 3,5-dinitro-2,6-bis-picrylamino pyridine (PYX), nitroglycerine (NG), ethylene glycol dinitrate (EGDN), ethylenedinitramine (EDNA), diethylene glycol dinitrate (DEGDN), Semtex, Pentolite, trimethylol ethyl trinitrate (TMETN), tetryl, hexahydro-1,3,5-trinitro-1,3,5-triazine (RDX), pentaerythritol tetranitrate (PETN) and 2,2,2-trinitroethyl-4,4,4-trinitrobutyrate (TNETB), methylamine nitrate, nitrocellulose, $N^3,N^3,N'^3,N'^3,N^7,N^7,N'^7,N'^7$-octafluoro-1,5-dinitro-1,5-diazocane-3,3,7,7-tetraamine (HNFX), nitroguanidine, hexanitrostilbene, 2,2-dinitroethene-1,1-diamin (FOX-7), dinitrourea, and picric acid. In various aspects, the energetic material is selected from the group consisting of 2,4,6-trinitrotoluene (TNT), and 1,3,5,7-tetranitro-1,3,5,7-tetrazocane (HMX)

In one embodiment, a cocrystal of CL-20 and 2,4,6-trinitrotoluene (TNT) has been prepared. The crystalline material contains CL-20 and TNT in a 1:1 ratio and presents as a single phase material.

Figure 1:
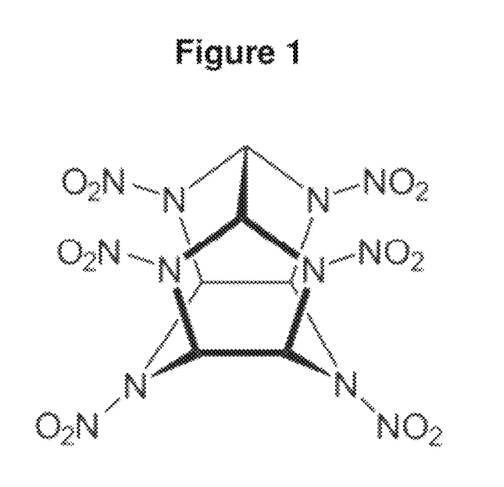
FIG. 1 shows the molecular structure of CL-20.

It is known that CL-20 can be prepared by condensing benzylamine and glyoxal in a solvent in the presence of a catalyst to produce hexabenzylhexaazaisowurtzitane (HBIW). HBIW is reductively acylated in the presence of a catalyst in a second step to produce dibenzyltetraacetylhexaazaisowurtzitane (TAIW). Finally, in the last step, TAIW is sequentially debenzylated and nitrated to produce CL-20. CL-20 exists as white/colorless crystals having a caged, 3-dimensional molecular structure. CL-20 exists in several forms, including alpha, beta, gamma, epsilon and zeta. The CL-20 chemical structure is illustrated in FIG. 1.

Figure 2:
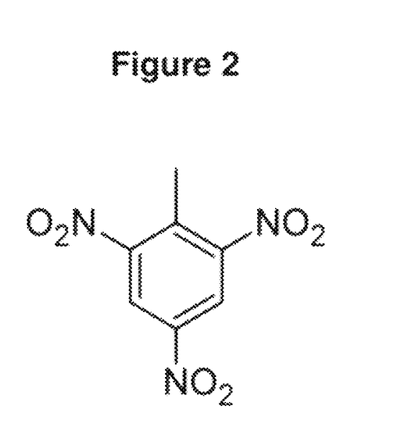
FIG. 2 shows the molecular structure of TNT.
Figure 3A:
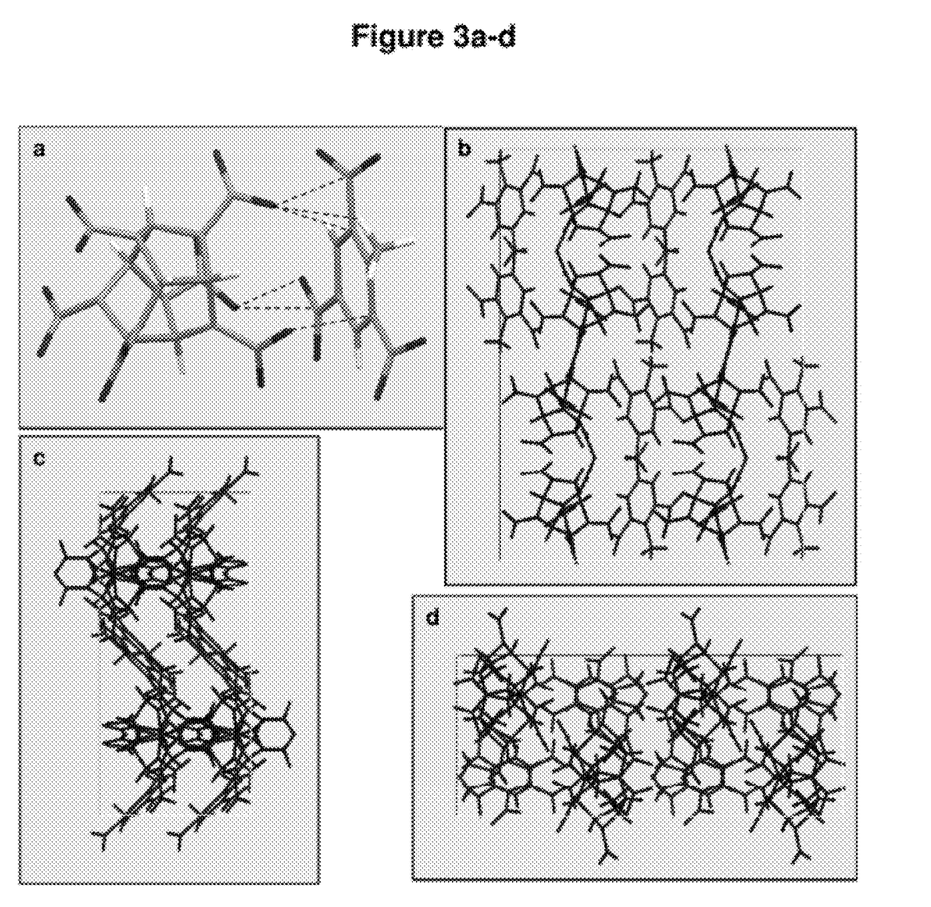

TNT crystals appear colorless to white or yellow. The presence of impurities in the crystals may result in the appearance of the yellowish color. It is known that TNT can be prepared by the nitration of toluene with a mixture of nitric acid and sulfuric acid. Toluene is nitrated in a three-step operation by using increasing temperatures and mixed-acid concentrations to successively introduce nitro groups to form mononitrotoluene (MNT), dinitrotoluene (DNT), and TNT. The nitration can be accomplished in three separate steps or by continuous flow. TNT exists in several polymorphs including monoclinic and orthorhombic forms. The TNT chemical structure is illustrated in FIG. 2.

In another embodiment, a cocrystal of CL-20 and 1,3,5,7-tetranitro-1,3,5,7-tetrazocane (HMX) has been prepared. The crystalline material contains CL-20 and HMX in a 2:1 ratio and presents as a single phase material.

Figure 7:
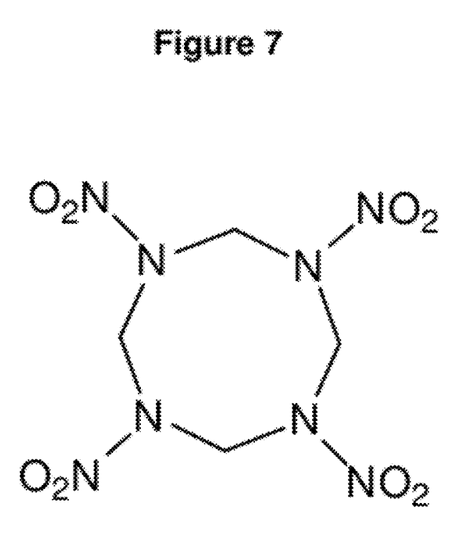
FIG. 7 shows the molecular structure of HMX.
Figure 8A:
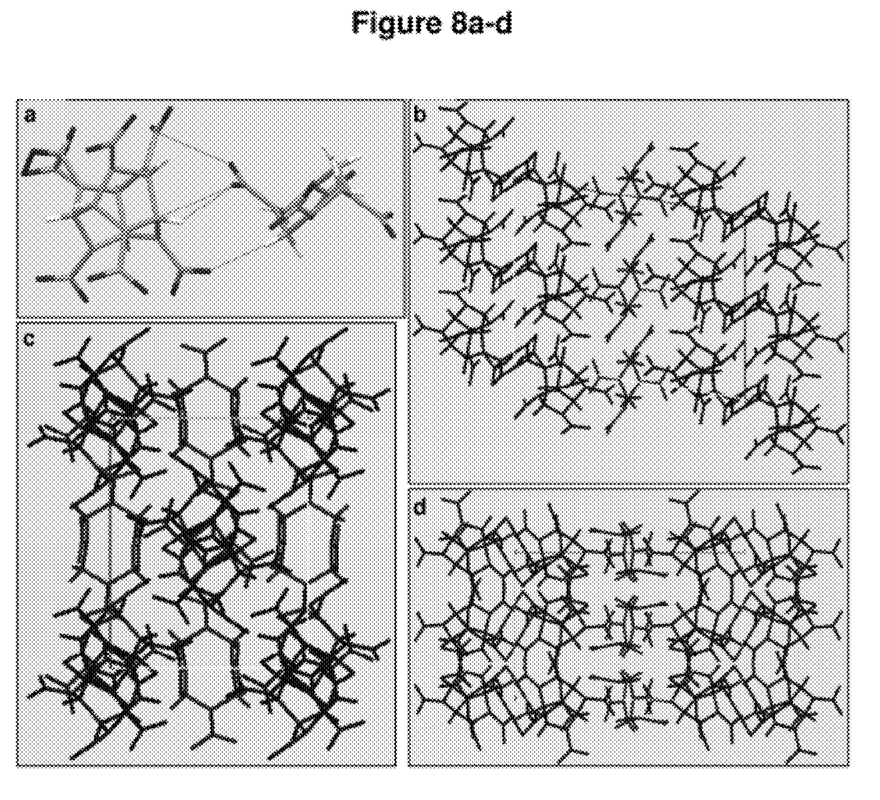

HMX, also referred to as octogen or cyclotetramethylenetetranitramine, exists as white/colorless crystals. It is a high explosive non-aromatic cyclic nitramine first mass-produced as a byproduct to 1,3,5-trinitro-1,3,5-triazinane (RDX) during World War II. Though HMX possesses sensitivity similar to RDX and explosive power slightly higher, it has only recently grown to rival RDX in terms of its use in military explosive applications. HMX is known to exist in several different forms such as alpha, beta, gamma and delta. The HMX chemical structure is illustrated in FIG. 7.

Assaying the solid phase for the presence of cocrystals of the CL-20 and the at least one energetic material can be carried out by conventional methods known in the art. For example, it is convenient and routine to use x-ray diffraction techniques to assess the presence of cocrystals. This may be effected by comparing the x-ray diffraction patterns of the CL-20, the energetic material, and recovered cocrystals in order to establish whether or not true cocrystals have been formed. Other comparable techniques include differential scanning calorimetry (DSC), thermogravimetric analysis (TGA), solid state NMR spectroscopy, infrared absorption spectrum (IR) and Raman spectroscopy. X-ray diffraction, infrared absorption spectrum (IR) and Raman spectroscopy are especially useful in identifying cocrystal structures. The X-ray powder diffraction pattern, infrared absorption spectrum (IR) and Raman spectroscopy of the cocrystals of the CL-20 and the at least one energetic material are determined using conventional techniques and equipment known to those skilled in the art of physical characterization.

In one aspect, the cocrystal is identified by determining at least one characteristic peak in an x-ray diffraction pattern. One of ordinary skill in the art understands that a crystal will exhibit an x-ray diffraction pattern and that the pattern provides peak positions and intensity. The peak positions are indicative of the crystal structure and symmetry of the crystal. The intensities are related to both the structure and composition of the crystal. A cocrystal (i.e. a crystalline material comprised of two or more unique materials) will produce an x-ray diffraction pattern that is different from the pattern of the individual materials. In the present application, the cocrystals exhibit patterns with unique sets of diffraction peaks that can be expressed in 2-theta angles (°), d-spacings (Å) and/or relative peak intensities different from CL-20 and the at least one energetic material individually. As is well known, there is a one to one correspondence between d-spacings and 2-theta values that depends on the wavelength of the x-rays used. Unless noted otherwise, $CuK_\alpha$ radiation (about 1.54 Å wavelength) is used herein. Equivalent values for other wavelengths can be readily calculated using the Bragg equation.

Cocrystal of CL-20 and TNT (1:1)

For example, the cocrystal of CL-20 and TNT is characterized as having an x-ray diffraction pattern comprising one or more peaks at about 8.85, 9.55, 12.36, 14.55, 17.75, 20.10, 21.55, 22.10, 27.15, 27.80, 28.30, and 28.95° 2-theta. In other embodiments, the cocrystal is characterized by an x-ray diffraction pattern with a 2-theta angle peak at 8.85° or 14.55°, all using $CuK_\alpha$ radiation. A typical x-ray diffraction pattern measured with $CuK_\alpha$ is illustrated in FIG. 4.

Figure 4:
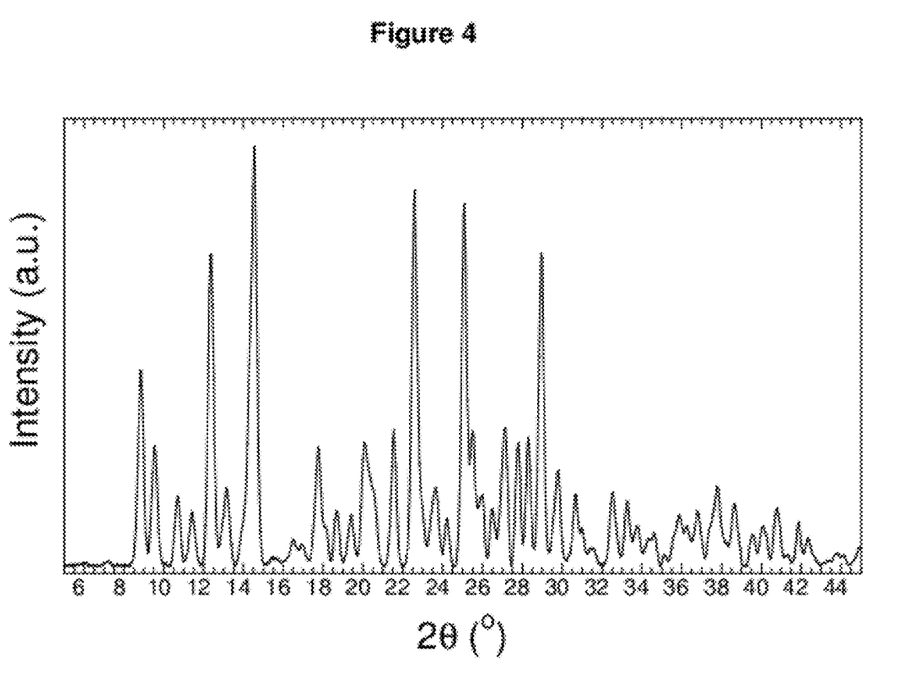
FIG. 4 illustrates an powder x-ray diffraction pattern of the cocrystal of CL-20 and TNT.

According to the pattern shown in FIG. 4, peaks can be seen at the 2-theta values given in Table 1. Of the peaks in Table 1, the 2-theta values at 8.85° and 14.55° are especially characteristic. It is understood that the 2-theta values given in Table 1 have an accuracy of ±0.10° or, in other aspects, an accuracy of ±0.20° 2-theta. That is, a peak in a diffraction pattern can be considered to overlap one given in Table 1 if the peak has a value of Table 1 ±0.20° or Table 1 ±0.10°.

TABLE 1

| X-ray Diffraction Pattern of CL-20:TNT 1:1 cocrystal | |
| --- | --- |
| Peak No. | 2-theta angle |
| 1. | 8.85 |
| 2. | 9.55 |
| 3. | 12.36 |
| 4. | 14.55 |
| 5. | 17.75 |
| 6. | 20.10 |
| 7. | 21.55 |
| 8. | 22.10 |
| 9. | 27.15 |
| 10. | 27.80 |
| 11. | 28.30 |
| 12. | 28.95 |

In one aspect, the cocrystal is identified by determining the wavenumber shifts of the Raman spectrum. Raman spectroscopy is a scattering technique wherein a light source, often a laser, is used to interact with a sample. The difference in energy between vibrational energy states and the ground state can be measured by determining the difference in energy between incident photons and scattered photons, a quantity known as the "Raman shift" or wavenumber shift. Because molecules can vibrate along many different directions (called "vibrational modes"), there is not a single excited vibrational state, but rather a multitude of them, with each vibrational mode represented by a different Raman shift. Therefore, every molecule has a unique Raman spectrum that may serve as a fingerprint to identify the molecule through its vibrational energy spectrum.

Figure 5:
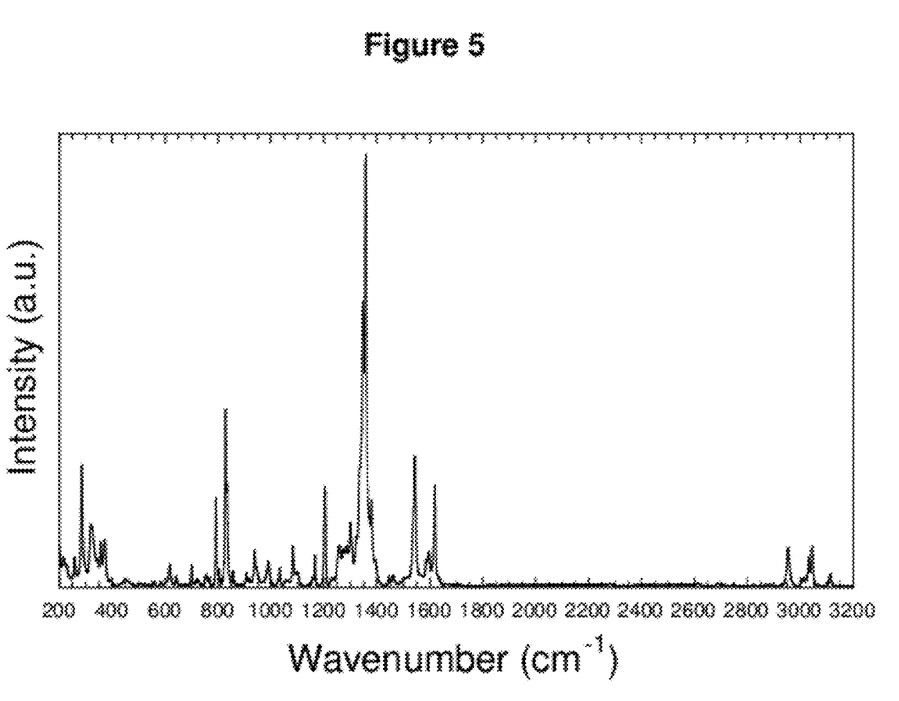
FIG. 5 illustrates a Raman spectrum of the cocrystal of CL-20 and TNT.

A characteristic Raman spectrum of the CL-20:TNT cocrystal material is given in FIG. 5, with the peaks listed in Table 2. The values of the frequencies in Table 2 for purposes of matching a measured spectrum are understood to have an accuracy of ±1 to ±5 cm$^{-1}$. That is, a peak in a Raman spectrum can be considered to overlap one given in Table 2 if the peak has a value of Table 2 ±1 cm$^{-1}$ or Table 2 ±5 cm$^{-1}$.

TABLE 2

Raman Spectrum Peaks of CL-20:TNT 1:1 cocrystal

| No. | Values cm$^{-1}$ |
| --- | --- |
| 1. | 792 |
| 2. | 878 |
| 3. | 1202 |
| 4. | 1537 |
| 5. | 1543 |
| 6. | 1618 |
| 7. | 2954 |
| 8. | 3033 |
| 9. | 3044 |

In another aspect, the cocrystal is identified by determining its infrared absorption spectrum. Similar to Raman spectroscopy, infrared spectroscopy measures the frequencies of infrared light absorbed by a crystal as a result of excitation of vibrational modes. The infrared spectrum of any molecule is a unique pattern of absorption wavelengths of varying intensity that can be considered as a molecular fingerprint to identify or characterize any compound.

Figure 6:
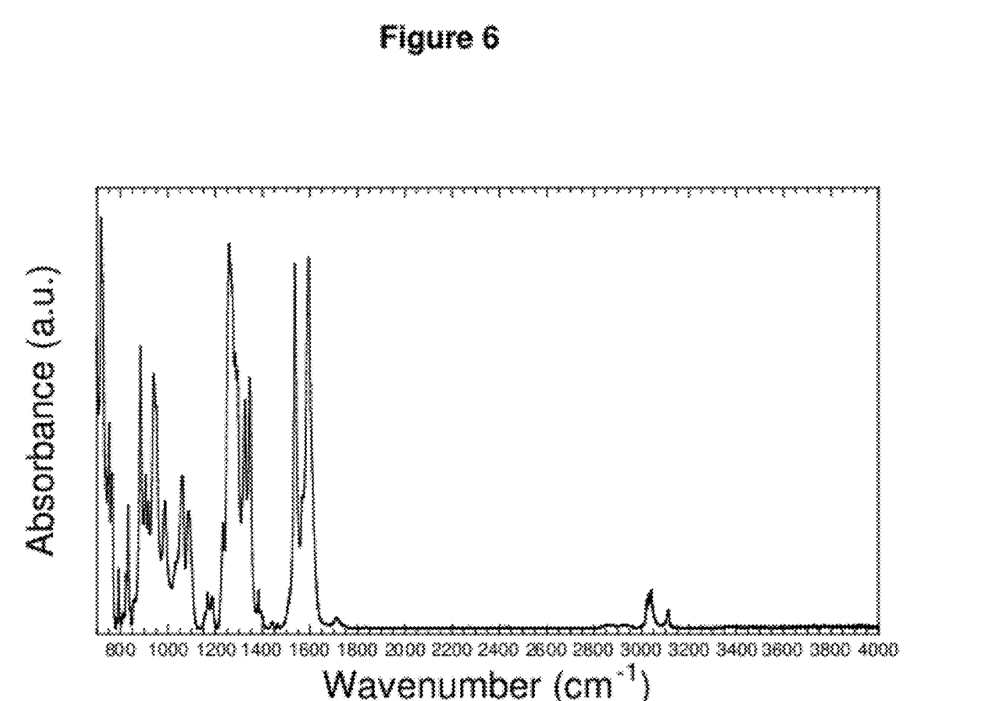
FIG. 6 illustrates an infrared absorption spectrum of the cocrystal of CL-20 and TNT.

Infrared absorption spectrum of the cocrystal material is given in FIG. 6, with peaks listed in Table 3, which are understood to have an accuracy of ±1 to ±5 cm$^{-1}$. That is, a peak in an infrared absorption spectrum can be considered to overlap one given in Table 3 if the peak has a value of Table 3 ±1 cm$^{-1}$ or Table 3 ±5 cm$^{-1}$.

TABLE 3

Infrared Absorption Spectrum

| No. | Values cm$^{-1}$ |
| --- | --- |
| 1. | 885 |
| 2. | 942 |
| 3. | 1061 |
| 4. | 1259 |
| 5. | 1346 |
| 6. | 1537 |
| 7. | 1594 |
| 8. | 3112 |

Figure 12:
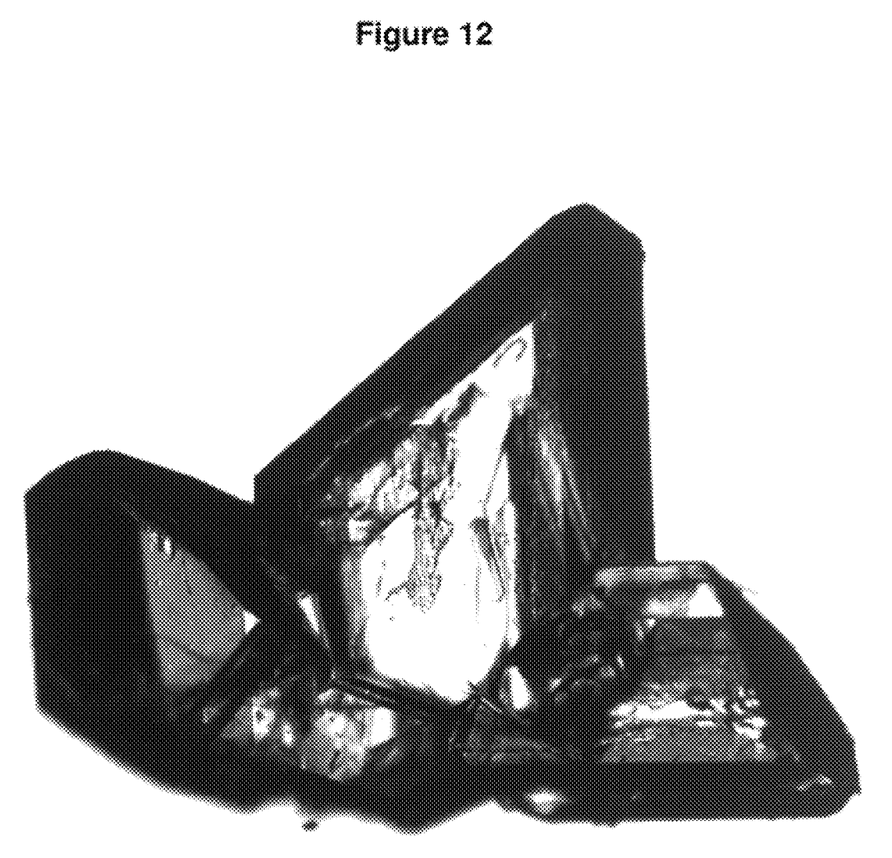
FIG. 12 is a photograph of the CL-20:TNT 1:1 cocrystal.

The cocrystal often takes a prismatic form visually different than the needle habit of TNT and, if in more subtle ways, distinguishable from the plate-like and imperfectly-faced rhomboids of α-CL-20, the most common pure CL-20 phase to nucleate from these solutions. In contrast, the cocrystals have clean faces and thick prismatic habits that will occasionally grow into thick needles (unlike the flat needles of TNT). CL-20, TNT, and the cocrystal appear colorless, but the presence of impurities can result in the individual crystals and cocrystal having yellowish color. A picture of the cocrystal of CL-20 and TNT is provided in FIG. 12.

The cocrystal can also be characterized by its crystallographic data. The characteristic crystallographic data are listed below in Table 4. FIGS. 3*a*-3*d* show a molecular model of the cocrystal of CL-20 and TNT.

TABLE 4

Crystallographic Data for 1:1 molar ratio CL-20:TNT cocrystal

| Formula | $C_{13}H_{11}N_{15}O_{18}$ |
| --- | --- |
| MW (g/mol) | 665.32 |
| stoichiometry | 1:1 |
| Color | Colorless |
| Morphology | Prism |
| Crystal System | orthorhombic |
| Space Group | Pbca |
| a (Å) | 9.67390(18) |
| b (Å) | 19.3690(4) |
| c (Å) | 24.6898(17) |
| α (deg) | 90.00 |
| β (deg) | 90.00 |
| γ (deg) | 90.00 |
| Cell Vol (Å$^3$) | 4626.22 |
| $\rho_{calc}$ (g/cm$^3$) | 1.910 |
| Z | 8 |
| Temp (K) | 95 |

The crystalline material containing CL-20 and TNT exhibits characteristic thermal properties. While CL-20 has a melting temperature of around 260° C. and TNT has a melting temperature of around 80° C., the 1:1 cocrystal converts to liquid TNT and solid CL-20 around 135° C.

Cocrystal of CL-20 and HMX

The CL-20:HMX cocrystal of the present invention is also characterized by its x-ray diffraction pattern, Raman spectrum, and infrared absorption spectrum. In one aspect, the cocrystal is characterized as a composition containing both CL-20 and HMX and having at least one characteristic peak in an x-ray diffraction pattern. For example, the cocrystal is characterized by an x-ray diffraction pattern having one or more peaks at about 10.85, 11.45, 13.22, 14.75, 18.53, 21.45, 24.40, 26.06, 27.81, 28.20, 29.72, 30.15, and/or 31.00° 2-theta. In other embodiments, the cocrystal is characterized by an x-ray diffraction pattern with a peak at 11.45°, 13.22, or 18.53° 2-theta, all using CuK$_\alpha$ radiation. A typical x-ray diffraction pattern is illustrated in FIG. 9.

Figure 9:
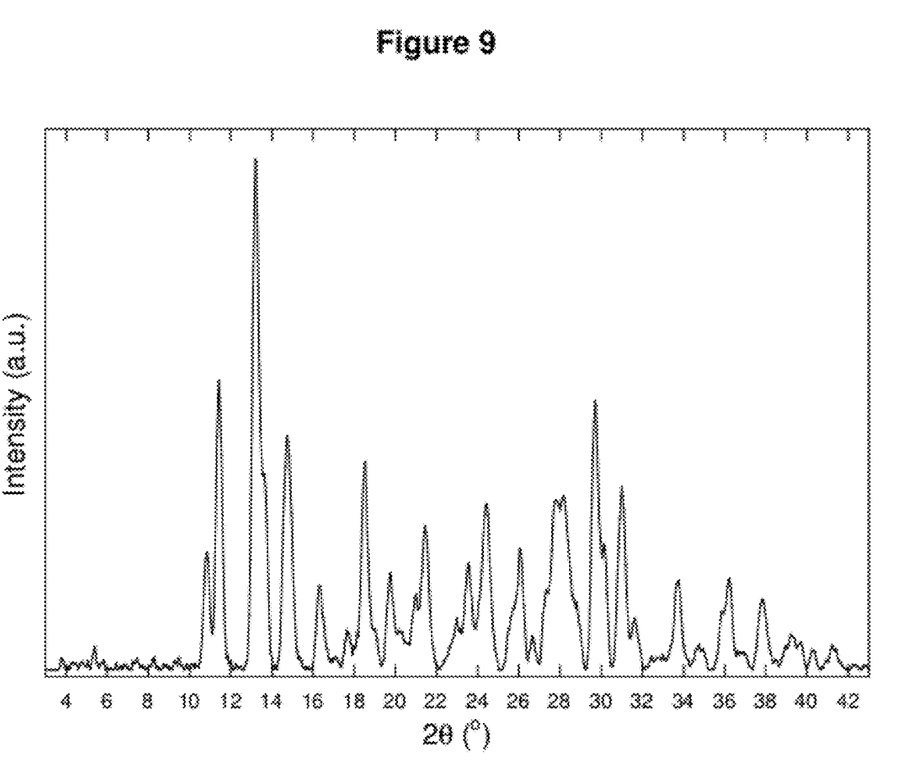
FIG. 9 illustrates an powder x-ray diffraction pattern of the cocrystal of CL-20 and HMX.

According to the pattern shown in FIG. 9, peaks can be seen at the 2-theta values given in Table 5. Of the peaks in Table 5, the 2-theta values at 11.45°, 13.22 and 18.53° are especially characteristic. It is understood that the 2-theta values given in Table 5 have an accuracy of ±0.10° or, in other aspects, an accuracy of ±0.20° 2-theta. That is, a peak in a diffraction pattern can be considered to overlap one given in Table 5 if the peak has a value of Table 5 ±0.20° or Table 5 ±0.10°.

TABLE 5

X-ray Diffraction Pattern

| Peak No. | 2-theta angle |
| --- | --- |
| 1. | 10.85 |
| 2. | 11.45 |
| 3. | 13.22 |
| 4. | 14.75 |
| 5. | 18.53 |
| 6. | 21.45 |
| 7. | 24.40 |
| 8. | 26.06 |
| 9. | 27.81 |
| 10. | 28.20 |
| 11. | 29.72 |
| 12. | 30.15 |
| 13. | 31.00 |

Figure 10:
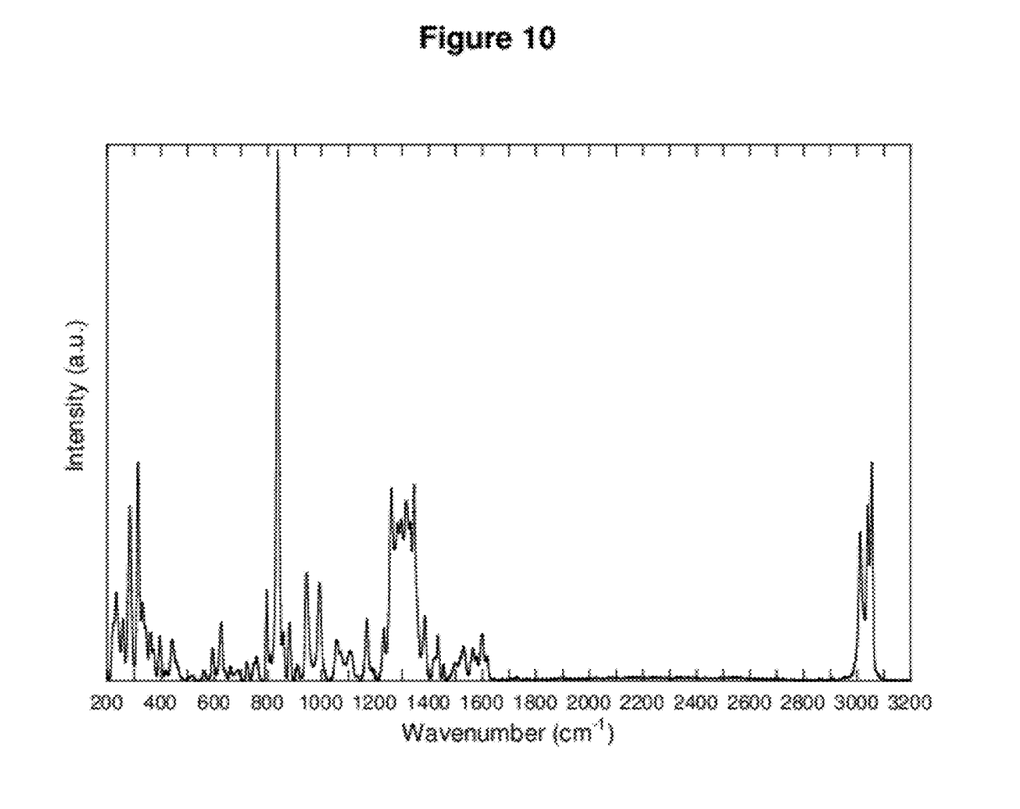
FIG. 10 illustrates a Raman spectrum of the cocrystal of CL-20 and HMX.

A further physical characteristic of the CL-20 and HMX cocrystal of the present invention includes its Raman spectrum, measured for example using a 647 nm laser. The cocrystal is characterized as having a Raman spectrum comprising one or more peaks at about 314, 836, 1260, 1282, 1316, 1344, 1578, 3012, 3039, and 3055 $cm^{-1}$. In other embodiments, the cocrystal is characterized at wavenumber shifts measured using a 647 nm laser at 836 and 3012 $cm^{-1}$. A typical Raman spectrum is illustrated in FIG. 10.

Peaks in the Raman spectrum are listed in Table 6. The values of the frequencies in Table 6 for purposes of matching a measured spectrum are understood to have an accuracy of ±1 to ±5 $cm^{-1}$. That is, a peak in a Raman spectrum can be considered to overlap one given in Table 6 if the peak has a value of Table 6 ±1 $cm^{-1}$ or Table 6 ±5 $cm^{-1}$.

TABLE 6

Raman Spectrum Peaks

| No. | Values $cm^{-1}$ |
|---|---|
| 1. | 314 |
| 2. | 836 |
| 3. | 1260 |
| 4. | 1282 |
| 5. | 1316 |
| 6. | 1344 |
| 7. | 1578 |
| 8. | 3012 |
| 9. | 3039 |
| 10. | 3055 |

Figure 11:
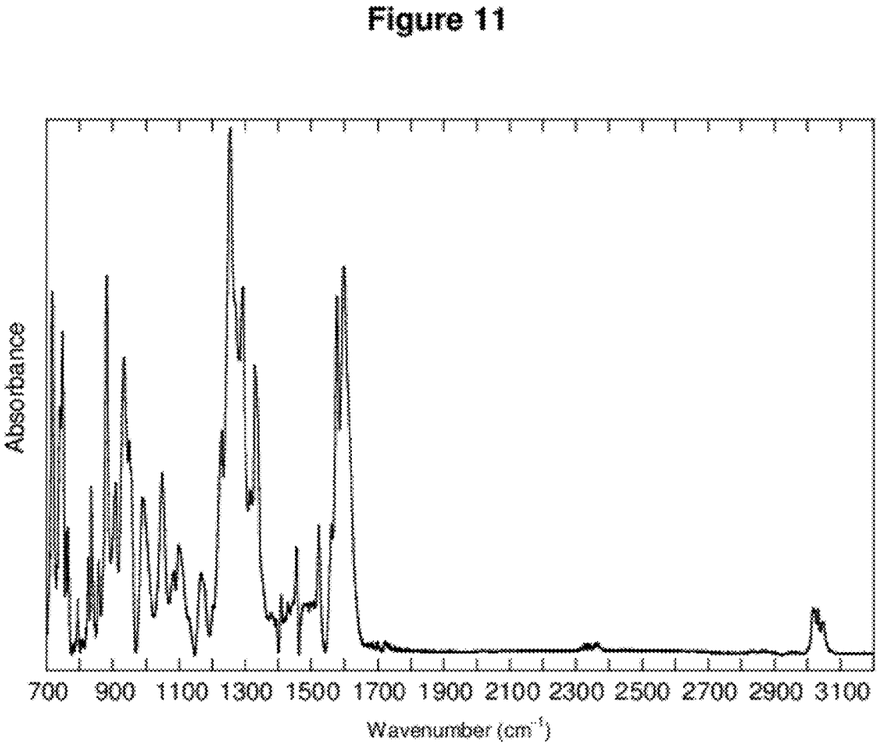
FIG. 11 illustrates an infrared absorption spectrum of the cocrystal of CL-20 and HMX.

A further characteristic of the CL-20 and HMX cocrystal of the present invention is its infrared absorption spectrum. The cocrystal is characterized has having an infrared absorption spectrum comprising one or more peaks at about 717, 748, 881, 933, 1254, 1292, 1330, 1577, 1598. 3017, 3032, and 3048 $cm^{-1}$. A typical infrared absorption spectrum is illustrated in FIG. 11.

Peaks listed in Table 7, are understood to have an accuracy of ±1 to ±5 $cm^{-1}$. That is, a peak in an infrared absorption spectrum can be considered to overlap one given in Table 7 if the peak has a value of Table 7 ±1 $cm^{-1}$ or Table 7 ±5 $cm^{-1}$.

TABLE 7

Infrared Absorption Spectrum

| No. | Values $cm^{-1}$ |
|---|---|
| 1. | 717 |
| 2. | 748 |
| 3. | 881 |
| 4. | 933 |
| 5. | 1254 |
| 6. | 1292 |
| 7. | 1330 |
| 8. | 1577 |
| 9. | 1598 |
| 10. | 3017 |
| 11. | 3032 |
| 12. | 3048 |

Figure 13:
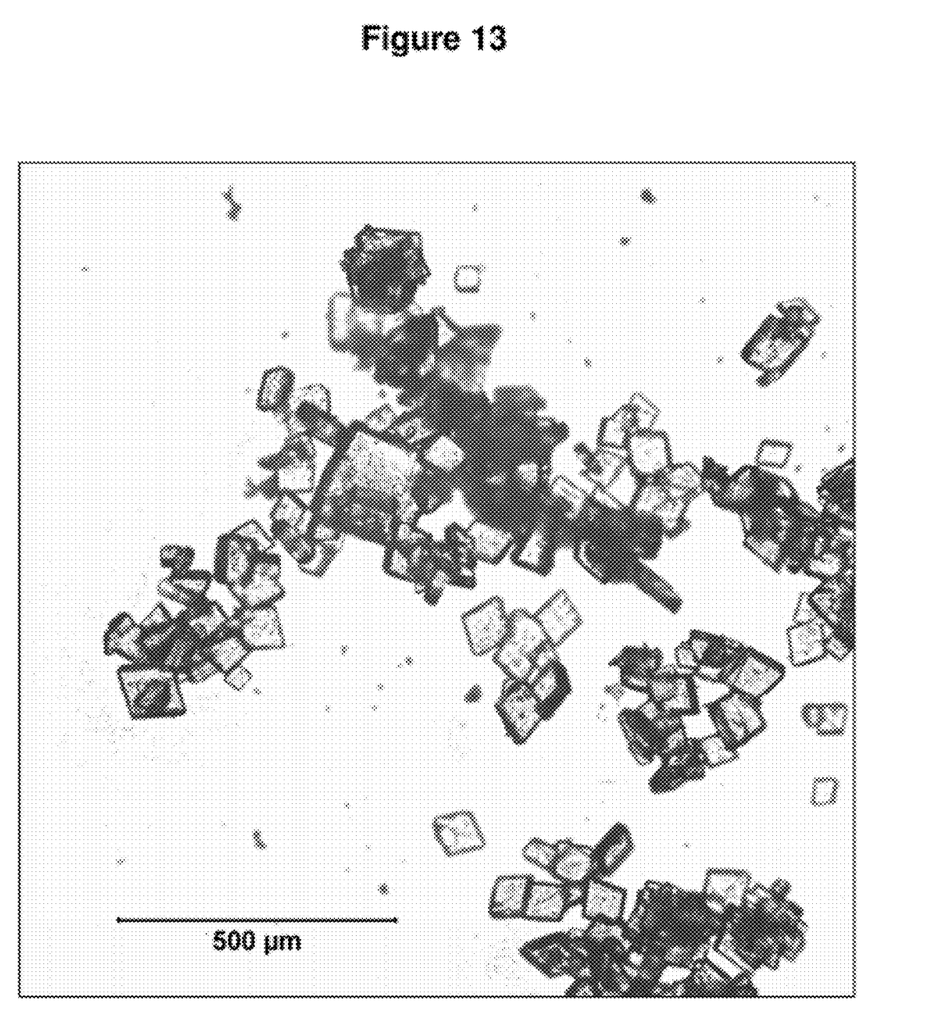
FIG. 13 is a photograph of the CL-20:HMX 2:1 cocrystal.

The cocrystal can take a rhomboid form visually different than the habits of pure HMX or CL-20. Though the cocrystals commonly appear as rhomboid plates, they are distinguishable from the plates of alpha-CL-20 by their angles. CL-20, HMX, and the cocrystal are white/colorless but impurities present may result in the crystals having a yellowish color. A picture of the cocrystal of CL-20 and HMX is provided in FIG. 13.

The cocrystal of CL-20 and HMX is also characterized by its crystallographic data. The cocrystal characteristic crystallographic data of the CL-20 and HMX is listed below in Table 8. FIGS. 8a-8d show a molecular model of the cocrystal of CL-20 and HMX

TABLE 8

Crystallographic Data for 2:1 molar ratio CL-20:HMX cocrystal

| Formula | $C_8H_{10}N_{16}O_{16}$ |
|---|---|
| MW (g/mol) | 586.27 |
| stoichiometry | 2:1 CL-20:HMX |
| Color | Colorless |
| Morphology | Rhomboid Plates |
| Crystal System | Monoclinic |
| Space Group | $P2_1/c$ |
| a (Å) | 16.3409(12) |
| b (Å) | 9.9338(5) |
| c (Å) | 12.1427(7) |
| α (deg) | 90 |
| β (deg) | 99.219(7) |
| γ (deg) | 90 |
| Cell Vol (Å$^3$) | 1945.63 |
| $\rho_{calc}$ (g/cm$^3$) | 2.00 |
| Z | 4 |
| Temp (K) | 95 |

The crystalline material containing CL-20 and HMX exhibits characteristic thermal properties. While CL-20 has a melting temperature of around 260° C. and HMX has a melting temperature of around 281° C., the cocrystal has a melting/decomposition temperature of around 235° C.

Synthesizing the Cocrystals

In various embodiments, a method for forming a cocrystal of CL-20 and at least one energetic material, involves evaporating a solution of CL-20 and the at least one energetic material in at least one organic solvent to form the cocrystal. In one embodiment, the cocrystal is formed by evaporating a solution of CL-20 (any form) and TNT (any form) in a number of dry organic solvents. Effort should be made to keep the solvent dry. Otherwise α-CL-20, a hydrate, can nucleate first and can prevent cocrystal formation. CL-20 and TNT are combined in a ratio that promotes the formation of a cocrystal by evaporation. In various embodiments, any form of CL-20 and any form of TNT are placed in a suitable solvent and dissolved. The solution can be gently heated for a short time at a low temperature or sonicated to aid in dissolution of CL-20 and TNT.

In various embodiments, a 1:1 molar ratio or molar excess of TNT is used. Growth from solutions containing excess TNT can produce a cocrystal reliably. In certain embodiments, excess TNT will form undesired pure TNT crystals along with the cocrystal. If desired, these can be removed with TNT-preferring solvents such as ethanol.

In another embodiment, the cocrystal can be formed by evaporating a solution of CL-20 (any form) and HMX (any form) in a number of organic solvents. CL-20 and HMX may be combined in a ratio that promotes the formation of a cocrystal by evaporation. In various embodiments, any form of CL-20, including the hydrate, and any form of HMX are placed in a suitable solvent and dissolved. The solution can be sonicated for a short time to aid in dissolution of CL-20 and HMX. After sonication, the solution can be decanted and filtered prior to evaporation. In various embodiments, the CL-20:HMX cocrystal formed is about 74.7 wt % CL-20 and about 25.3 wt % HMX. The cocrystal has an oxygen balance of about −13.7% and a crystallographic density of about 2.00 g/cm$^3$ (at 95 K).

Examples of solvents effective for cocrystal formation include acetone, anisole, ethanol, formic acid, ethyl formate, cumene, acetic acid, isobutyl acetate, isopropyl acetate, ethyl acetate, butyl acetate, propyl acetate, methyl acetate, propanoic acid, diethyl ether, t-butyl methyl ether, 1-butanol, 2-butanol, 1-propanol, 2-propanol, heptane, 1-pentanol, 4-methyl-2-pentanone, 2-butanone, 3-methyl-1-butanol, 2-methyl-1-propanol, tetrahydrofuran, acetonitrile, cyclohexane, 1,2-dimethoxyethane, 1,4-dioxane, 2-ethoxyethanol, hexane, pentane, methanol, isopropanol, 2-ethoxymethanol, methylcyclohexane, tetralin, toluene, xylene, water, hexane, cyclohexane, heptane, toluene, xylene, methanol, absolute ethanol, ethanol, and mixtures thereof.

The evaporation time is not particularly limited but can be a matter of minutes, hours, a day, or up to 5 days depending on the conditions. In various embodiments, after the solvent has evaporated, the resulting cocrystal solid can be recovered by conventional means well known to those skilled in the art such as centrifugation, washing, i.e. purifying, dehydration, filtration or a combination thereof.

There is no particular restriction on the temperature, evaporation condition, or time before recovery after the start of crystallization of the cocrystal. Since these conditions may affect the yield, chemical purity, particle size, or the like of crystals, however, these conditions can be adjusted in combination according to the purpose.

Cocrystals of CL-20 and TNT from Slurry

In various embodiments, a method for forming a cocrystal of CL-20 and at least one energetic material comprises combining CL-20 and the at least one energetic material in a solvent to form a slurry; agitating the slurry; removing the solvent from the slurry; and recovering the cocrystal of CL-20 and the at least one energetic material.

In another embodiment, the cocrystal can also be generated through solvent-mediated solid state conversions. In various embodiments, a slurry comprising CL-20 and TNT is used to form cocrystals. Any form of CL-20, including the hydrate, and any form of TNT are placed in a suitable solvent to form a slurry. A slurry is formed when less solvent is added than is required to dissolve all of the components.

In various embodiments, to obtain a cocrystal of CL-20 and TNT through solvent-mediated solid state conversions, it is effective to add a seed of the cocrystal to the slurry. The amount of the seed crystals is generally about 0.01% to about 20% of the slurry. In various embodiments, the seed crystals are ground or milled prior to being added to the slurry.

Cocrystals of CL-20 and HMX from Slurry

Likewise, in various embodiments, a slurry comprising CL-20 and HMX is used to form cocrystals. Any form of CL-20, including the hydrate, and any form of HMX are placed in a suitable solvent to form a slurry. A slurry is formed when less solvent is added than is required to dissolve all of the components.

In various embodiments, to obtain a cocrystal of CL-20 and HMX through solvent-mediated solid state conversions, it is effective to add a seed of the cocrystal to the slurry. The amount of the seed crystals is generally about 0.01% to about 20% of the slurry. In various embodiments, the seed crystals may be ground or milled prior to being added to the slurry. The cocrystal seed are ground or milled by techniques known in the art.

In various embodiments, the slurry is then agitated such as by shaking or stirring to speed up the conversion of the solids from starting components to the cocrystal. The agitation time varies with the nature of the solvent, the scale of the experiment, and the ambient conditions, among others. At the end of the agitation time, the solvent is removed, for example by evaporation, from the vial. The evaporation time is not particularly limited but can be a matter of minutes, hours, a day or up to 3 days, depending on the conditions. The cocrystal of CL-20 and HMX may also be prepared by, for example, freeze drying, quench cooling, rapid evaporation of, or rapid cooling of, a solution of CL-20 and HMX in an appropriate solvent.

Forming Cocrystals

In various embodiments, the resulting cocrystal solid can be recovered by conventional means well known to those skilled in the art such as centrifugation, washing, i.e. purifying, dehydration, filtration or a combination thereof. In various embodiments, a dehydrating agent is added to the slurry to aid in the recovery of the cocrystal. The dehydrating agents include 3A, 4A and 5A molecular sieves.

Depending on these conditions, cocrystals form from the starting components in a matter of minutes, hours, or days. In exemplary embodiments, a cocrystal forms within 1 day, 2 days, or 3 days. In a non-limiting example, a sample of roughly 300 milligrams total mass converts entirely to cocrystal in roughly two days. Considerably wet solvents will tend to produce the hydrated α-CL-20 instead of the desired cocrystal. Therefore dry solvents are preferred. Suitable dry solvents can be prepared in known ways and stored over known drying agents and/or in inert atmospheres.

There is no particular restriction on the temperature, evaporation condition, agitation condition or time before recovery after the start of crystallization of the cocrystal. Since these conditions may affect the yield, chemical purity, particle size, or the like of crystals, however, these conditions can be adjusted in combination according to the purpose.

Thus in various embodiments, the present disclosure provides a complex of CL-20 and at least one energetic material in a crystalline form. In various embodiments, the present disclosure provides a 1:1 complex of CL-20 and TNT in a crystalline form. In other embodiments, the present disclosure provides a 2:1 complex of CL-20 and HMX in a crystalline form. Explosive compositions contain the complex and one or more other explosive materials or additives. The crystalline material described herein can be used in munitions, propellants, and demolition applications according to known methods. The crystalline material may also be used as energetic filler or propellant component in weapons systems to provide increased anti-armor penetration, enhanced missile payload velocity and flight, increased underwater torpedo effectiveness and lethality, improved gun propellant impetus, and mining and blasting applications. In use, the CL-20/HMX cocrystalline material has the advantage that it is less shock sensitive if compared to CL-20 and a more powerful explosive (i.e., higher detonation velocity etc.) than HMX.

Formulations Using the Cocrystals

The crystalline material containing CL-20 and the energetic material can be used alone or in combination with other explosive materials. In one embodiment, the cocrystalline material containing CL-20 and TNT (1:1) is provided in substantially pure form and in combination with one or more group A initiating explosives. In another embodiment, the cocrystalline material containing CL-20 and HMX (2:1) is provided in substantially pure form and in combination with one or more group A initiating explosives. Such compositions include, without limitation, combinations of the CL-20 and at least one energetic material cocrystal with one or more of CL-20, CP (5-Cyanotetrazolpentaamine Cobalt III perchlorate), dry HMX (Cyclotetramethylene tetranitramine), lead azide, lead stiffnate, mercury fulminate, dry nitrocellulose, dry PETN (Pentaerythritol tetranitrate), dry RDX (Cyclotrimethylene trinitramine), TATNB (Triazidotrinitrobenzene), dry HMX (Cyclotetramethylene tetranitramine).

In other embodiments, the crystalline material containing a complex of CL-20 and at least one energetic material can be combined with one or more Group D explosives (explosives without their own means of initiation). In one embodiment, the cocrystalline material containing CL-20 and TNT (1:1) is provided in substantially pure form and in combination with one or more Group D initiating explosives. In another embodiment, the cocrystalline material containing CL-20 and HMX (2:1) is provided in substantially pure form and in combination with one or more Group D initiating explosives. Without limitation these include combinations of the CL-20 and at least one energetic material cocrystal with one or more of ammonium picrate, baratol, black powder, boracitol, wet CL-20 (Hexanitrohexaazaisowurtzitane), cyclotols (≤85% RDX), DATB (Diaminotrinitrobenzene), bis-Dinitropropyl adipate, bis-Dinitropropyl glutarate, bis-Dinitropropyl maleate, Dinitropropane, Dinitropropanol, Dinitropropyl acrylate monomer (DNPA), Dinitroproply acrylate polymer (PD-NPA), Explosive D, GAP (Glyceryl azide polymer), wet or dry HNS (Hexanitrostilbene), Methyl dinitropentanoate, NG/TA (Nitroglycerine-triacetine), wet Nitrocellulose, Nitroguanidine (NQ), Octol (≥75% HMX), Pentolite, wet PETN (Pentaerythritol tetranitrate), PETN/extrudable binder, PGN (Polyglycidyl nitrate), Plastic-bonded explosive, PBX (a SC/HC Group D formulated with a desensitizing binder), Potassium picrate, wet RDX (Cyclotrimethylene trinitramine), TATB (Triamino trinitrobenzene), TATB/DATB mixtures, TEGDN (Triethylene glycol dinitrate), TMETN (Trimethylolethane trinitrate), TNAZ (Trinitoazetidine), and TNT (Trinitrotoluene).

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

EXAMPLES

Example 1

A glass vial is loaded with 4.38 mg of CL-20 (10 µmol, any pure form or the alpha-hydrate), 2.27 mg of TNT (10 µmol, monoclinic), and 1 mL of ethanol. Mild heating is used to dissolve all CL-20. The vial cap is loosened to allow for slow evaporation of the solvent. After five days colorless prismatic crystals have formed on the vial bottom. Upon complete evaporation of the solvent, a mass of 1:1 CL-20:TNT cocrystal rests at the bottom of the vial in polycrystalline clusters.

Example 2

A glass vial is loaded with 4.38 mg of CL-20 (10 µmol, any pure form or the alpha-hydrate) and 2.27 mg of TNT (10 µmol, monoclinic), and 0.5 mL of acetonitrile, dissolving the CL-20 and TNT. The vial cap is loosened to allow for slow evaporation of the solvent. After one day the solvent is evaporated. A mass of 1:1 CL-20:TNT cocrystal rests at the bottom of the vial in small polycrystalline clusters. Some portions of the cocrystal appear clear and glassy, but give spectra (both Raman and PXRD) that identify it as the cocrystal.

Example 3

A glass vial is loaded with 166.1 mg of CL-20 (0.38 mmol, any pure form or the alpha-hydrate) and 86.1 mg of TNT (0.38 mmol, monoclinic) along with 1 mL of 2-proponal (insufficient to completely dissolve either the CL-20 or TNT) and four beads of 4A molecular sieve (activated in by 60 seconds of microwave radiation). The slurry is sealed and shaken gently for three days. In that time the needle habits of pure TNT disappear. At the end of three days the solvent is removed by evaporation from the vial. Polycrystalline 1:1 CL-20:TNT cocrystal is the only solid form detected in the sample.

Example 4

Masses of 4.18 mg of epsilon-CL-20 (10 µmol) and 1.48 mg of beta-HMX (5 µmol) are placed in a glass vial along with 5 mL of toluene. Sonication is used to facilitate dissolution prior to the liquid portion being decanted and filtered with a 0.45 µm PTFE filter. The vial cap is loosened to allow for slow evaporation of the solvent. After three days at room temperature colorless rhomboid plates have formed on the vial bottom. Upon complete evaporation of the solvent, a mass of 2:1 CL20:HMX cocrystal rests at the bottom of the vial as these plates as well as polycrystalline clusters. These are determined to be the 2:1 CL-20:HMX cocrystal by Raman spectroscopy as well as by powder x-ray diffraction.

Example 5

Masses of 4.18 mg of epsilon-CL-20 (10 µmol) and 1.48 mg of beta-HMX (5 µmol) are placed in a glass vial along with 5 mL of isopropanol. Sonication is used to facilitate dissolution prior to the liquid portion being decanted and filtered with a 0.45 µm PTFE filter. The vial cap is loosened to allow for slow evaporation of the solvent and a single bead of freshly activated 4A molecular sieve is added to the solution. After three days at room temperature colorless rhomboid plates have formed on the vial bottom. Upon complete evaporation of the solvent, a mass of 2:1 CL-20:HMX cocrystal rests at the bottom of the vial as these plates. These are determined to be the 2:1 CL-20:HMX cocrystal by Raman spectroscopy as well as by powder x-ray diffraction.

Example 6

Masses of 0.74 mg of epsilon-CL-20 (1.77 µmol) and 0.26 mg of beta-HMX (0.89 µmol) occupy a well in a 96-well polypropylene plate with 100 µL of 2-propanol (insufficient to completely dissolve either the CL-20 or HMX). The slurry is sealed and shaken gently for five days. In that time the thick prismatic habits of pure CL-20 and HMX disappear as clear rhomboid plates appear. These are determined to be the 2:1 CL-20:HMX cocrystal by Raman spectroscopy as well as by single crystal and powder x-ray diffraction.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A cocrystal of 2,4,6,8,10,12-hexanitro-2,4,6,8,10,12-hexaazaisowurtzitane and at least one energetic material.

2. The cocrystal of claim 1, wherein the energetic material is selected from the group consisting of 2,4,6-trinitrotoluene and 1,3,5,7-tetranitro-1,3,5,7-tetrazocane.

3. A 1:1 cocrystal of 2,4,6,8,10,12-hexanitro-2,4,6,8,10,12-hexaazaisowurtzitane and 2,4,6-trinitrotoluene.

4. The cocrystal of claim 3, wherein the cocrystal is characterized by an x-ray pattern having at least one of the following 2-theta angle peaks using $CuK_\alpha$ radiation: 8.85, 9.55, 12.36, 14.55, 17.75, 20.10, 21.55, 22.10, 27.15, 27.80, 28.30, and 28.95°.

5. The cocrystal of claim 4, wherein the cocrystal is characterized by an x-ray diffraction peak at 2-theta values of 8.85° or 14.55° using $CuK_\alpha$ radiation.

6. The cocrystal of claim 3, wherein the cocrystal is characterized by a Raman spectrum with a peak at one or more of the following wavenumber shifts measured using a 647 nm laser: 792, 878, 1202, 1537, 1543, 1618, 2954, 3033, and 3044 $cm^{-1}$ wavenumbers.

7. The cocrystal of claim 3, wherein the cocrystal is characterized by having an infrared absorption spectrum containing one or more of the following wavenumber absorptions: 885, 942, 1061, 1259, 1346, 1537, 1594, and 3112 $cm^{-1}$ wavenumbers.

8. The cocrystal of claim 3, wherein the cocrystal is characterized by a conversion to its pure components at a temperature of about 135° C.

9. An explosive composition comprising the cocrystal of claim 3.

10. A 2:1 cocrystal of 2,4,6,8,10,12-hexanitro-2,4,6,8,10,12-hexaazaisowurtzitane and 1,3,5,7-tetranitro-1,3,5,7-tetrazocane.

11. The cocrystal of claim 10, wherein the cocrystal is characterized by an x-ray pattern having at least one of the following 2-theta angle peaks using $CuK_\alpha$ radiation: 10.85, 11.45, 13.22, 14.75, 18.53, 21.45, 24.40, 26.06, 27.81, 28.20, 29.72, 30.15, and 31.00°.

12. The cocrystal of claim 11, wherein the cocrystal is characterized by an x-ray diffraction peak at 2-theta values of 11.45°, 13.22°, or 18.53° using $CuK_\alpha$ radiation.

13. The cocrystal of claim 10, wherein the cocrystal is characterized by a Raman spectrum with a peak at one or more of the following wavenumber shifts measured using a 647 nm laser: 314, 836, 1260, 1282, 1316, 1344, 1578, 3012, 3039, and 3055 $cm^{-1}$ wavenumbers.

14. The cocrystal of claim 13, wherein the cocrystal is characterized by a Raman spectrum containing the following wavenumber shifts measured using a 647 nm laser: 836 and 3012 $cm^{-1}$.

15. The cocrystal of claim 10, wherein the cocrystal is characterized by having one or more of the following wavenumber shifts containing one or more of the following wavenumber absorptions: 717, 748, 881, 933, 1254, 1292, 1330, 1577, 1598, 3017, 3032, and 3048 $cm^{-1}$ wavenumbers.

16. The cocrystal of claim 15, wherein the cocrystal is characterized by an infrared spectrum containing the following wavenumber shifts: 1254 and 1598 $cm^{-1}$.

17. The cocrystal of claim 10 wherein the cocrystal is characterized by a melting/decomposition point of about 235° C.

18. An explosive composition comprising the cocrystal of claim 10.

* * * * *